(12) United States Patent
Tokudome et al.

(10) Patent No.: US 7,197,359 B1
(45) Date of Patent: *Mar. 27, 2007

(54) COMPOSITIONS FOR ELECTROPORATION

(75) Inventors: Yoshihiro Tokudome, Yokohama (JP); Koji Owaku, Yokohama (JP); Kenichi Goto, Yokohama (JP); Kenji Sugibayashi, Kawagoe (JP)

(73) Assignee: Pola Chemical Industries Inc., Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/110,712

(22) PCT Filed: Apr. 6, 2000

(86) PCT No.: PCT/JP00/02243

§ 371 (c)(1), (2), (4) Date: Apr. 11, 2002

(87) PCT Pub. No.: WO01/26687

PCT Pub. Date: Apr. 19, 2001

(30) Foreign Application Priority Data

Oct. 14, 1999 (JP) ................................. 11-291733

(51) Int. Cl.
*A61N 1/30* (2006.01)

(52) U.S. Cl. .................. 604/20; 424/448; 424/449

(58) Field of Classification Search ............ 604/65–67, 604/890.1, 891.1, 30, 31, 50, 20, 289, 61; 424/443–449; 607/120, 39, 43, 20
See application file for complete search history.

(56) References Cited

U.S. PATENT DOCUMENTS

| 4,933,184 | A | | 6/1990 | Tsuk |
| 5,019,034 | A | * | 5/1991 | Weaver et al. ................. 604/20 |
| 5,069,908 | A | | 12/1991 | Henley |
| 5,990,179 | A | | 11/1999 | Gyory et al. |
| 5,997,501 | A | * | 12/1999 | Gross et al. ................... 604/65 |
| 6,248,349 | B1 | * | 6/2001 | Suzuki et al. ................ 424/449 |
| 6,266,560 | B1 | * | 7/2001 | Zhang et al. .................. 604/20 |
| 6,302,874 | B1 | | 10/2001 | Zhang et al. |
| 6,527,759 | B1 | * | 3/2003 | Tachibana et al. ........... 604/500 |
| 6,532,386 | B2 | * | 3/2003 | Sun et al. ...................... 604/20 |
| 6,678,558 | B1 | * | 1/2004 | Dimmer et al. ................. 607/3 |
| 6,697,669 | B2 | | 2/2004 | Dev et al. |
| 6,743,432 | B1 | * | 6/2004 | Yanai et al. ................. 424/400 |

FOREIGN PATENT DOCUMENTS

| DE | 39 25 680 A1 | 2/1991 |
| GB | 2 239 600 | 7/1991 |
| JP | 09-255561 | 9/1997 |

(Continued)

OTHER PUBLICATIONS

Sun, *Skin Absorption Enhancement by Physical Means: Heat, Ultrasound, and Electricity*, "Transdermal and Topical Drug Delivery Systems," Ghosh, et al., 1997, Interpharm Press, pp. 327-355.
Supplementary European Search Report completed on Jan. 12, 2005 and issued to a related foreign application.

*Primary Examiner*—Kevin C. Sirmons
*Assistant Examiner*—Laura C. Schell
(74) *Attorney, Agent, or Firm*—Knobbe, Martens, Olson & Bear, LLP

(57) ABSTRACT

The present invention relates to compositions for electroporation which are useful in elevating percutaneous absorbability of drugs, etc. By controlling electrolyte concentration of compositions for electroporation so as to make an osmotic pressure of the compositions not more than a physical osmotic pressure, the percutaneous absorbability of drugs can be elevated.

4 Claims, 1 Drawing Sheet

FOREIGN PATENT DOCUMENTS

| WO | WO 89/06555 | 7/1989 |
|----|-------------|--------|
| WO | WO 94/21117 | 9/1994 |
| WO | WO 95/26781 | 10/1995 |
| WO | WO 96/30078 | 10/1996 |
| WO | WO 96/32155 | 10/1996 |
| WO | WO 96/39422 | 12/1996 |

* cited by examiner

COMPOSITIONS FOR ELECTROPORATION

CROSS-REFERENCE TO RELATED APPLICATIONS

This is the National Phase under 35 U.S.C. § 371 of International Application No. PCT/JP00/02243, filed Apr. 6, 2000, which claims priority to Japanese Patent Application No. 11/291733 filed Oct. 14, 1999. The International Application was published under PCT Article 21(2) in a language other than English.

BACKGROUND OF THE INVENTION

1. Field of the Invention

The present invention relates to compositions for electroporation which are useful for elevating percutaneous absorbability of drugs, etc. The present invention is useful in the field of drugs.

2. Description of the Related Art

Although percutaneous absorption route has been expected as an administration route for drugs since it gives less pain than injection does and in addition it involves less possibility of forgetting to administrate drugs than oral administration does, it is rather difficult to allow percutaneous absorption due to a preventive function that the skin inherently has so that under the present circumstances the percutaneous absorption route has not been established yet as means for delivering drugs. As one devised method in order to overcome the present problem, a so-called electroporation may be exemplified according to which pores are formed in the skin structure by application of a voltage and a drug is delivered through such pores. Recently, it has become clear that in such an electroporation, the behavior of drugs is different from that in ordinary administration so that it has been desired to develop compositions for percutaneous administration which are suitable for such an electroporation. That is, although electroporation is a means which is useful for percutaneous delivery of a drug, this alone is insufficient for the delivery of a drug in some cases and coming on the market of a pharmaceutical preparation that can elevate this effect has been desired.

On the other hand, little has been yet known on the influence of electrolyte such as a salt comprised in a composition for electroporation in electroporation. Therefore, nothing has been known on the fact that a preparation comprising substantially no such electrolyte is excellent in the effect of delivering an active ingredient by electroporation and on the fact that, due to coexistence of monoterpene, polyhydric alcohol or the like together with it, effect is further elevated.

SUMMARY OF THE INVENTION

Under the aforementioned circumstances, the present invention has been made and is aimed at providing a composition for percutaneous administration which is suitable for electroporation.

In consideration of the circumstances, the present inventors have made extensive studies in pursuit of a composition for percutaneous administration which is suitable for electroporation in order to elevate the percutaneous permeability of drugs and as a result the inventors have found that such preparations can be produced by adjusting the concentration of electrolytes so as to make its osmotic pressure equal to or lower than physiological osmotic pressure, thus achieving the present invention. Further studies have led to the discovery that addition of monoterpene or polyhydric alcohol further elevates such permeability and further advanced the invention. That is, the present invention provides compositions for electroporation having a concentration of electrolyte adjusted so as to make its osmotic pressure below physiological osmotic pressure. In addition, it provides compositions for electroporation preferably further comprising monoterpene or polyhydric alcohol.

(1) Osmotic Pressure of the Composition for Electroporation of the Present Invention The composition for electroporation of the present invention has an osmotic pressure, which is equal to or lower than physiological osmotic pressure. That is, in the case where physiological saline is used as the standard for physiological osmotic pressure, the osmotic pressure is adjusted so as to be equal to physiological osmotic pressure by addition of 0.9% sodium chloride, which is the electrolyte used for physiological saline. In contrast, in an electroporation of the present invention, an osmotic pressure is adjusted to a level lower than this. That is, the electroporation of the present invention is characterized in that the content of substantial electrolytes, inclusive of an active ingredient, is not higher than the chemical equivalent of sodium chloride in the physiological saline. Here, the term substantial means taking dissociation constant into consideration since the concentration of an electrolyte is an issue. In other words, electrolytes having smaller dissociation constants may be comprised in larger amounts accordingly. In practice, the extent of osmotic pressure of the composition may be determined by examining whether or not the osmotic pressure is lower or higher than that of physiological saline by use of a semipermeable membrane such as cellophane. By adjusting the osmotic pressure in this manner, the percutaneous permeability of drugs can be further elevated by utilizing osmotic pressure in addition to electroporation. Further, limiting the amount of electrolyte results in limiting the effect of closing pores generated by electroporation of the electrolyte and is advantageous in this respect as well. Therefore, as a most preferable embodiment is an embodiment in which no electrolyte other than active ingredients is comprised.

(2) Preferred Components of the Composition for Electroporation of the Present Invention The composition for electroporation of the present invention preferably comprises polyhydric alcohol. As the polyhydric alcohol that can be used in the composition for electroporation of the present invention, any polyhydric alcohol can be used without any particular limitation as far as it is usually used in similar fields such as skin external agents. Preferred examples thereof include polyethylene glycol, 1,3-butanediol, propylene glycol, glycerol, dipropylene glycol, diglycerol, sorbitol, maltitol and the like. Among these, one or more selected from propylene glycol, glycerol, polyethylene glycol and 1,3-butanediol are preferred. It is preferred that they are in a liquid state at 25° C. and at 1 atm and have a molecular weight on the order of 80 to 200. This is because percutaneous absorbability elevates under such conditions in electroporation. Among these, a more preferred polyhydric alcohol is glycerol and/or propylene glycol. It is particularly preferred that the polyhydric alcohol consists of this only. This is because it is a component excellent in elevating particularly percutaneous absorbability in electroporation and at the same time has many utilization track records as the skin external agents, and its properties on safety have already been grasped. In the composition for electroporation of the present invention, a preferred content of the polyhydric alcohol is 1 to 90% by weight and more preferably 5 to 30% by weight. This value has been set up in consideration of safety of the polyhydric alcohol, degree of freedom in selecting optional components in preparation forms of the composition, effective dose of the active ingredients, and optimal amount for percutaneous absorption promoting effect.

It is preferred that the composition for electroporation of the present invention further comprises monoterpene. Preferred examples of the monoterpene include menthol and its optical isomers, menthone, thymol, etc. Among these, menthol is preferred and l-menthol is more preferred. This is because, among monoterpenes, menthols, in particular l-menthol are excellent particularly in percutaneous absorption promoting effect in the electroporation of the present invention. In the composition for electroporation of the present invention, a preferred content of monoterpenes is 0.1 to 10% by weight and more preferably 0.5 to 5% by weight. This is because, if the monoterpenes are present too much, they cause irritation in some cases and if they are present too little, no percutaneous absorption promoting effect can be obtained in some cases.

(3) Compositions for Electroporation According to the Present Invention

The compositions for electroporation of the present invention may comprise besides preferred components, i.e., polyhydric alcohol and monoterpenes, optional components for manufacturing pharmaceutical preparations which are used for ordinary compositions for electroporation in a range satisfying the above-mentioned essential condition. Preferred examples of such optional components include, for example, hydrocarbons such as squalene, vaseline, microcrystalline wax, esters such as jojoba oil, carnauba wax, and octyldodecyl oleic acid, triglycerides such as olive oil, beef tallow, and coconut oil, fatty acids such as stearic acid, oleic acid and ricinoleic acid, higher alcohols such as oleyl alcohol, stearyl alcohol, and octyldodecanol, anionic surfactants such as sulfosuccinic acid esters and sodium polyoxyethylenealkylsulfate, amphoteric surfactants such as alkyl-betaine salts, cationic surfactants such as dialkylammonium salts, nonionic surfactants such as sorbitan fatty acid esters, fatty acid monoglycerides, polyoxyethylene adducts of these, polyoxyethylene alkyl ethers and polyoxyethylene fatty acid esters, viscosity bodying and gelling agents, antioxidants, ultraviolet absorbents, coloring agents, preservatives, powders and the like. Further, as drugs that are percutaneously administered by such an electroporation, those usually used as medical preparations can be applied without any particular limitation. For example, analgesic antipyretic anti-inflammatory agents such as codeine, morphine, hydromorphone, oxycodone, pethidine, buprenorphin hydrochloride, pentazocine, and tramadol hydrochloride, protein-based drugs such as insulin, carcitonin, elcatonin, adrenocorticotrophic hormone (ACTH), parathyroid hormone (PTH), selectin, oxytocin, angiotensin, β-endorphin, vasopressin, glucagon, somatostatin, luteinizing hormone-releasing hormone (LH-RH), enkephalin, neurotensin, atrial sodium diuretic peptide (ANP), growth hormone, bradykinin, substance P, dynorphin, thyroid stimulating hormone (TSH), prolactin, G-CSF, glutathione peroxidase, superoxide dismutase (SOD), desmopressin, somatomedin, melanocyte stimulating hormone (MSH), calcitonin gene related peptide (CGRP), endothelin, and thyrotropin releasing hormone (TRH), interleukins, interferons, anti-platelet drugs, vasodilaters, argatroban as anti-arteriosclerotic drug, sarpogrelate hydrochloride, sodium beraprost, limaprost alfadex, and cilostazol and the like. These drugs must be administered with passage of time by necessary amounts so that they are agreeable to the properties of percutaneous administration. The compositions for electroporation of the present invention are processed into preparation forms in conformity with the physical properties of the active ingredients, such as solutions, emulsions, semi-solids, and solids, by treating the aforementioned essential components, preferred components, optional components and active ingredients according to the conventional method, and are used in electroporation. That is, by using the compositions of the present invention, drugs as active ingredients can be percutaneously administered by electroporation. Upon electroporation, they are used together with a device for electroporation. Among the aforementioned preparation forms, preferred preparation forms include aqueous preparation forms and particularly preferred are an aqueous solution preparation form, aqueous gel preparation form and emulsion preparation form.

(4) Skin External Drug Administration Unit of the Present Invention

The unit for administrating drugs for external application to the skin of the present invention includes the composition for electroporation and a device for electroporation of the present invention in combination. The device for electroporation is not particularly limited as far as it is used usually in such a use, and for example, those devices described in Japanese Domestic Patent Laid Open Publication No. Hei 11-507341 (laying open of a Japanese translation), Japanese Domestic Patent Laid Open Publication No. Hei 11-505445 (laying open of a Japanese translation), Japanese Domestic Patent Laid Open Publication No. Hei 10-502827 (laying open of a Japanese translation), Japanese Domestic Patent Laid Open Publication No. Hei 11-503349 (laying open of a Japanese translation), Japanese Domestic Patent Laid Open Publication No. Hei 08-511680 (laying open of a Japanese translation), Japanese Domestic Patent Laid Open Publication No. Hei 03-502416 (laying open of a Japanese translation), etc. may be used. Further, those commercially available devices for such an electroporation include ECM-600 produced by BTX Co., GENE PULSER produced by BIO-RAD Co., etc. Also, these may be used. The electroporation may be performed under conditions similar to the conventionally known conditions and the conditions may be changed as appropriate.

BEST MODE FOR CARRYING OUT THE INVENTION

Figure 1:
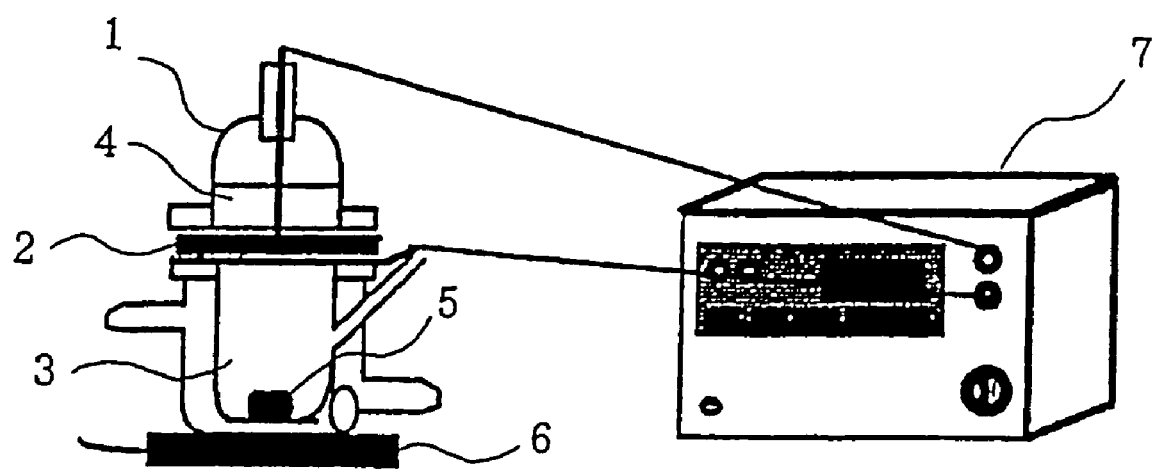
FIG. 1 is a diagram showing the apparatus for electroporation used in Examples 1 and 2.

Hereinafter, the present invention will be described in more detail by way of examples. Of course, the present invention is not limited to the examples.

Examples 1 and 2

According to the recipes shown in Table 1 below, compositions for electroporation of the present invention were prepared. As a model labeled drug, 1 mM sodium calcein was used. These were stirred and solubilized to prepare compositions (liquid agents) for electroporation of the present invention. The compositions for electroporation were measured of their percutaneous absorption promoting effect by a percutaneous permeability test by using a Franz cell. More particularly, to a Franz cell 1, a skin sample 2 which had been obtained from the abdominal part of a hairless rat and from which subcutaneous fat had been removed was attached as a separator with the keratin layer directed toward the donor side. The receiver side was filled with physiological saline 3 while the donor side was filled with 3 mL of the composition 4 for electroporation of the present invention. The receiver side was stirred at 1,200 rpm by a stirrer 6 by use of a star-head type stirrer 5. Each 0.3 ml aliquot was collected with passage of time and the same amount of physiological saline was added and percutaneous permeability was examined. The amount of sodium calcein was measured by using a fluorometer. The electroporation was conducted under the conditions of using GENE PULSER produced by BIO-RAD Co. as a pulse voltage generator 7 at 300 V at a capacitance of a capacitor of 25 µF with applying 10 pulses (0.5 minute intervals) in first 5 minutes out of 60 minutes and turning off the voltage for the remaining 55 minutes. The results are shown in Table 1 in terms of cumulative permeation amount for 6 hours (nmol/cm$^2$). From this, it can be seen that percutaneous permeability is promoted in a range in which the osmotic pressure of composition is equal to or lower than a physiological osmotic pressure. This apparatus is shown in FIG. 1.

TABLE 1

| Example | Recipe | | Cumulative permeation amount |
|---|---|---|---|
| Example 1 | Sodium chloride<br>sodium calcein<br>Water | 0.9% by weight<br>1 mM<br>Balance | 2.53 |
| Example 2 | sodium calcein<br>Water | 1 mM<br>Balance | 15.02 |

Examples 3 to 6

Compositions (liquid agents) for electroporation of the present invention were produced by varying the concentration of propylene glycol according to the recipes shown below. That is, the components in the recipes were stirred and solubilized to obtain compositions. These were measured of cumulative permeation amount for 1 to 3 hours in the same manner as in Examples 1 and 2. The results are shown in Table 2. From this, it can be seen that an optimal concentration exists for the polyhydric alcohol and the content of polyhydric alcohol is preferably 5 to 30% by weight.

TABLE 2

| Example | Recipe | | One-hour cumulative amount | Two-hour cumulative amount | Three-hour cumulative amount |
|---|---|---|---|---|---|
| Example 3 | sodium calcein<br>Propylene glycol<br>Water | 1 mM<br>10% by weight<br>90% by weight | 46.8 | 147.8 | 328.8 |
| Example 4 | sodium calcein<br>Propylene glycol | 1 mM<br>25% by weight | 34.6 | 112.0 | 245.8 |
| Example 5 | sodium calcein<br>Propylene glycol<br>Water | 1 mM<br>50% by weight<br>50% by weight | 7.7 | 32.0 | 73.7 |
| Example 6 | sodium calcein<br>Propylene glycol | 1 mM<br>100% by weight | 9.1 | 27.0 | 36.2 |

Example 7

According to the recipe shown below, a composition for electroporation of the present invention was prepared. That is, the components in the recipe were stirred and solubilized to obtain a composition for electroporation. This had a cumulative drug permeation amount of 25.2 in 1 hour, 138.9 in 2 hours and 388.8 in 3 hours, which revealed that it is preferable that the composition comprises monoterpene.

| Water | 47 parts by weight |
|---|---|
| sodium calcein | 1 mM |
| Propylene glycol | 50 parts by weight |
| Menthol | 3 parts by weight |

Example 8

According to the recipe shown below, a composition for electroporation of the present invention was prepared. That is, the components in the recipe were stirred and solubilized to obtain a composition for electroporation. This had a cumulative drug permeation amount of 13.4 in 1 hour, 73.1 in 2 hours and 179.7 in 3 hours, in which revealed that glycerin is also preferable as polyhydric alcohol.

| Water | 50 parts by weight |
|---|---|
| sodium calcein | 1 mM |
| glycerin | 50 parts by weight |

Example 9

According to the recipe shown below, a composition for electroporation of the present invention was prepared. That is, the components in the recipe were stirred and solubilized to obtain a composition for electroporation.

| Water | 69 parts by weight |
|---|---|
| Buprenorphin hydrochloride | 1 part by weight |
| glycerin | 30 parts by weight |

Example 10

According to the recipe shown below, a composition for electroporation of the present invention was prepared. That is, the components in the recipe were stirred and solubilized to obtain a composition for electroporation.

| | |
|---|---|
| Water | 69 parts by weight |
| Buprenorphin hydrochloride | 1 part by weight |
| Propylene glycol | 30 parts by weight |

Example 11

According to the recipe shown below, a composition for electroporation of the present invention was prepared. That is, the components in the recipe were stirred and solubilized to obtain a composition for electroporation.

| | |
|---|---|
| Water | 69 parts by weight |
| Insulin | 1 part by weight |
| Propylene glycol | 30 parts by weight |

Example 12

According to the recipe shown below, a composition for electroporation of the present invention was prepared. That is, the recipe component A was added to the recipe component B and the mixture was stirred, dispersed and solubilized to obtain a composition (emulsion) for electroporation.

| A | |
|---|---|
| Phosphatidylcholine | 30 parts by weight |
| Cholesterol | 30 parts by weight |

| B | |
|---|---|
| Buprenorphin hydrochloride | 1 part by weight |
| Water | 39 parts by weight |

INDUSTRIAL APPLICABILITY

According to the present invention, a composition for percutaneous administration which is suitable for electroporation can be provided and the present invention is useful in the field of drugs.

What is claimed is:

1. A method for administrating a drug, comprising the steps of:
    preparing a composition which consists essentially of the drug, an electrolyte, 5 to 30% by weight of polyhydric alcohol, and menthol;
    adjusting the concentration of the drug and the electrolyte so that an osmotic pressure of the composition is lower than the osmotic pressure of physiological saline, whereby percutaneous drug absorbability is elevated;
    applying the composition to skin;
    impressing voltage temporarily to the skin during treatment with a device for electroporation; and
    contacting the composition to the skin without applying the voltage during the remaining time of the treatment, thereby elevating a percutaneous absorbability of the drug to the skin and permeating the drug to the skin.

2. The method for administrating the drug according to claim 1, wherein the polyhydric alcohol is propylene glycol.

3. The method for administrating the drug according to claim 1, wherein impressing voltage temporarily to the skin is conducted at 300 V at a capacitance of 25 µF within 5 min.

4. The method for administrating the drug according to claim 1, wherein time of contacting the composition to the skin without applying the voltage is 55 min.

* * * * *